United States Patent
Fu et al.

(10) Patent No.: US 12,272,082 B2
(45) Date of Patent: Apr. 8, 2025

(54) METHOD AND SYSTEM FOR CONSTRUCTING BONE MODEL, MEDIUM AND DEVICE

(71) Applicants: Vostro Medical Technology (Tianjin) Co., Ltd, Tianjin Pilot Free Trade Zone (CN); Mingjun Fu, Henan Province (CN); The Fourth Medical Center of PLA General Hospital, Beijing (CN)

(72) Inventors: Mingjun Fu, Tianjin (CN); Wei Chai, Beijing (CN); Yuan Zhang, Chongqing (CN); Mingmin Ren, Tianjin (CN); Guoqing Yu, Tianjin (CN); Linshuai He, Tianjin (CN); Mingcheng Shen, Tianjin (CN); Zhongwei Wang, Tianjin (CN); Chengcheng Shang, Tianjin (CN)

(73) Assignees: Vostro Medical Technology (Tianjin) Co., Ltd, Tianjin Pilot Free Trade Zone (CN); Mingjun Fu, Henan Province (CN); The Fourth Medical Center of PLA General Hospital, Beijing (CN)

( * ) Notice: Subject to any disclaimer, the term of this patent is extended or adjusted under 35 U.S.C. 154(b) by 0 days.

(21) Appl. No.: 18/603,869

(22) Filed: Mar. 13, 2024

(65) Prior Publication Data
US 2024/0420353 A1   Dec. 19, 2024

(30) Foreign Application Priority Data

Jun. 15, 2023   (CN) .......................... 202310705769.2

(51) Int. Cl.
G06T 15/00    (2011.01)
G06T 7/33     (2017.01)
(Continued)

(52) U.S. Cl.
CPC .............. *G06T 7/344* (2017.01); *G06T 17/00* (2013.01); *G06T 19/20* (2013.01); *G16H 50/50* (2018.01);
(Continued)

(58) Field of Classification Search
CPC . G06T 17/00; G06T 7/13; G06T 2207/30008; Y02T 10/40
(Continued)

(56) References Cited

U.S. PATENT DOCUMENTS 9,740,960 B2 *  8/2017  Van Lierde ............... G06T 7/10
11,132,833 B2 *  9/2021  Fedyukov ................. G06T 7/50
(Continued)

FOREIGN PATENT DOCUMENTS

CN    105608741 A    5/2016
CN    109978998 A    7/2019
(Continued)

OTHER PUBLICATIONS

Suwarganda EK, Diamond LE, Lloyd DG, Besier TF, Zhang J, Killen BA, Savage TN, Saxby DJ. Minimal medical imaging can accurately reconstruct geometric bone models for musculoskeletal models. PloS one. Feb. 1, 20191;14(2):e0205628.*

(Continued)

*Primary Examiner* — Phu K Nguyen
(74) *Attorney, Agent, or Firm* — Bay State IP, LLC

(57) ABSTRACT

The disclosed method includes acquiring sample models and marking sample feature points; selecting target feature points and regional points on bones; transforming the target feature points and the regional points, and registering the target feature points with the sample feature points; formulating a strategy for assigning impact factors to the sample models, linearly combining all sample models to construct an initial model, and determining initial feature points (Continued)

corresponding to the target feature points in the initial model; adjusting the strategy according to the distance between initial feature points and the target feature points, selecting the strategy corresponding to the minimum distance as an optimal strategy, and determining an optimal initial model; determining a matching point corresponding to each regional point in the optimal initial model, and calculating a transformation relationship; and transmitting all points of the optimal initial model according to the transformation relationship to obtain a target bone model.

10 Claims, 6 Drawing Sheets

(51) Int. Cl.
  *G06T 17/00* (2006.01)
  *G06T 19/20* (2011.01)
  *G16H 50/50* (2018.01)
  *A61B 34/10* (2016.01)

(52) U.S. Cl.
  CPC ......... *A61B 34/10* (2016.02); *A61B 2034/105* (2016.02); *G06T 2207/30008* (2013.01); *G06T 2207/30204* (2013.01); *G06T 2210/41* (2013.01); *G06T 2219/2004* (2013.01)

(58) Field of Classification Search
  USPC ........................................................ 345/418
  See application file for complete search history.

(56) References Cited

U.S. PATENT DOCUMENTS

| 11,426,281 | B2 | 8/2022 | Mahfouz |
| 2011/0044521 | A1* | 2/2011 | Tewfik .................... G06T 7/251 |
| | | | 382/131 |
| 2014/0161334 | A1 | 6/2014 | Wang et al. |
| 2021/0012492 | A1 | 1/2021 | Karade |
| 2021/0082179 | A1* | 3/2021 | Fedyukov ................. G06T 7/60 |
| 2021/0090694 | A1* | 3/2021 | Colley .................... G16H 15/00 |
| 2022/0187841 | A1* | 6/2022 | Ebrahimi Afrouzi ....... |
| | | | G05D 1/0274 |
| 2023/0146649 | A1 | 5/2023 | Wang et al. |
| 2023/0169727 | A1 | 6/2023 | Sminchisescu et al. |
| 2024/0193770 | A1* | 6/2024 | Lee ....................... G06T 7/0012 |

FOREIGN PATENT DOCUMENTS

| CN | 110570464 A | 12/2019 |
| CN | 110570515 A | 12/2019 |
| CN | 111640175 A | 9/2020 |
| CN | 114332378 A | 4/2022 |
| WO | 2023078309 A1 | 5/2023 |

OTHER PUBLICATIONS

Heimann T, Meinzer HP. Statistical shape models for 3D medical image segmentation: a review. Medical image analysis. Aug. 1, 2009;13(4):543-63.*

* cited by examiner

METHOD AND SYSTEM FOR CONSTRUCTING BONE MODEL, MEDIUM AND DEVICE

CROSS REFERENCE TO RELATED APPLICATION

This patent application claims the benefit and priority of Chinese Patent Application No. 202310705769.2, filed with the China National Intellectual Property Administration on Jun. 15, 2023, the disclosure of which is incorporated by reference herein in its entirety as part of the present application.

TECHNICAL FIELD

The present disclosure relates to the technical field of intelligent healthcare, and in particular to a method and system for constructing a bone model, a medium, and a device.

BACKGROUND

Computed tomography (CT) is an advanced technology for medical imaging using X-rays. The basic principle of this technology is that an X-ray transmitter and a detector rotate around a scanned object to obtain X-ray penetration information from multiple angles. Afterwards, the data are input into a computer for processing and analyzing to generate a transverse (i.e., tomographic) image of the scanned region. Such a tomographic image can clearly show various structures inside the human body, including bones, muscles and organs, and thus plays an important role in medical diagnosis and surgical planning.

However, the dependence of CT scanning on X-rays means that the CT scanning can produce a certain radiation to human body, and this radiation has attracted the attention of people. Therefore, in order to ensure the safety of medical practitioners, especially patients, there are strict regulations and controls on the radiation dose used in CT scanning in the medical industry. The radiation dose of CT scanning will be accurately adjusted according to the age and weight of the patient, and the scanned sites. When deciding whether to have a CT scan, doctors will carefully consider the balance between the diagnostic benefits and possible radiation risks, and will choose to have a CT scan only when the diagnostic benefits outweigh the radiation risks. In addition, the need for a separate appointment for the CT scan may increase the financial burden of patients and reduce the efficiency of hospital beds, leading to the increase of the surgical cycle.

At the same time, although the CT scan has been widely used in medicine, there are still some challenges in its application in joint replacement and other surgeries. For doctors, the first step of accurate joint replacement surgery is to make a detailed and accurate preoperative plan. Although many planning strategies at present rely on CT scanning images, the CT scanning is relatively weak in capturing articular cartilage information, and it is impossible to obtain accurate bone and cartilage information to achieve cartilage and bone reconstruction. During the surgery, if there is no accurate cartilage information, it is impossible to make an accurate osteotomy path, which will affect the preoperative planning and increase the surgical risk of the patient.

In the prior art, three-dimensional reconstruction is mostly carried out through the data from different modality imaging (including DICOM (Digital Imaging and Communications in Medicine) from MRI/CT (Magnetic resonance imaging/Computed tomography), X-ray images and ultrasound) based on the spatial attributes of image pixels (such as edges and regional contours), so as to obtain a three-dimensional bone model of the patient. However, the bone reconstruction effect of this method may vary greatly with different data, resulting in unsatisfactory surgical effect, and the advanced AI (artificial intelligence) segmentation method, which relies on a lot of data training, requires high computer performance.

In addition, specifically, cartilage surface reconstruction method and registration method are disclosed in the patents CN109692041A and CN115239830A. These two methods are based on the information of hard bone surfaces, and then spatial coordinate information of the registration point of the hard bone surface in the real world is obtained through an optical positioning system. This process includes two stages: firstly, a rough registration is carried out to align the positions of the virtual and real hard bone surfaces; and secondly, multiple points are collected on the cartilage surface to execute precise registration, so as to obtain cartilage surface information.

Although the cartilage surface information can be constructed using the above two methods, there are still some defects. This process needs to obtain the hard bone surface information of the patient first, which means that the patient still needs to be examined by CT before surgery, and CT examination not only increases the radiation to the patient, but also prolongs the diagnosis and treatment time and increases the economic cost. In addition, in the rough registration stage, in the process of collecting the hard bone surface information in the real world, it is necessary to pierce the cartilage surface to obtain the information of points under the cartilage surface. This operation may not only destroy the actual cartilage surface of the patient, but also introduce human errors, which affects the collection accuracy of the point, and then brings errors to the subsequent registration and model construction, affecting the accuracy of preoperative planning made by the doctors.

SUMMARY

Based on this, for the problems above, a method and system for constructing a bone model, a medium and a device are provided by the present disclosure.

In a first aspect, a method for constructing a bone model disclosed by the present disclosure includes the following steps:
  acquiring multiple sample bone models, and marking sample feature points in the sample bone models;
  selecting target feature points and target regional points on real bones of a patient, and recording positions of the target feature points and the target regional points under an image coordinate system, where the target feature points are points, corresponding to the sample feature points, on the real bones of the patient, and the target regional points are points in key regions needed for bone model construction;
  performing spatial transformation on the target feature points and the target regional points under the image coordinate system according to the positions of the target feature points and the target regional points under the image coordinate system, so as to register the target feature points with the sample feature points in any sample bone model under a same coordinate system;
  formulating an impact factor assignment strategy for assigning an impact factor for each sample bone model, and linearly combining all sample bone models according to the impact factor assignment strategy to construct an initial target bone model, and determining initial feature points corresponding to the target feature points in the initial target bone model;

adjusting the impact factor assignment strategy according to distance between the initial feature points and the corresponding target feature points, selecting an impact factor assignment strategy corresponding to the minimum distance as an optimal impact factor assignment strategy, and determining an optimal initial target bone model according to the optimal impact factor assignment strategy; and determining a matching point corresponding to each target regional point in the optimal initial target bone model, calculating a transformation relationship between the target regional point and the corresponding matching point, and performing spatial transformation on all points in the optimal initial target bone model according to the transformation relationship, so as to obtain a final target bone model.

Further, performing spatial transformation on the target feature points and the target regional points under the image coordinate system to make the target feature points register with the sample feature points in any sample bone model under a same coordinate system specifically includes the following steps:

performing spatial transformation on the target feature points and the target regional points under the image coordinate system by means of an ICP (Iterative Closest Point) registration algorithm, so as to register the target feature points with the sample feature points in any sample bone model under the same coordinate system.

Further, adjusting the impact factor assignment strategy according to distance between the initial feature points and the corresponding target feature points, selecting an impact factor assignment strategy corresponding to the minimum distance as an optimal impact factor assignment strategy, and determining an optimal initial target bone model according to the optimal impact factor assignment strategy specifically include the following steps:

initializing an optimal initial target bone model variable for storing the constructed optimal initial target bone model;

initializing a minimum distance mean variable, presetting a minimum distance mean, and storing a minimum distance mean in the minimum distance mean variable;

traversing and searching the impact factor assignment strategy through a searching strategy;

for the currently searched impact factor assignment strategy, linearly combining all sample bone models to construct a current initial target bone model, and determining current initial feature points corresponding to the target feature points in the current initial target bone model;

initializing a distance sum variable for calculating a distance sum between the target feature points and the current initial feature points;

traversing each target feature point;

calculating Euclidean distance between a current target feature point and the current initial feature point;

accumulating the calculated Euclidean distance into the distance sum variable;

dividing the distance sum variable by the number of the target feature points to calculate the distance mean corresponding to the current impact factor assignment strategy;

comparing the distance mean corresponding to the current impact factor assignment strategy with the minimum distance mean;

if the distance mean corresponding to the current impact factor assignment strategy is less than the minimum distance mean, storing the current initial target bone model in the optimal initial target bone model variable, and updating the minimum distance mean variable to the distance mean corresponding to the current impact factor assignment strategy; and after completing the search of the impact factor assignment strategy, taking the model stored in the optimal initial target bone model variable as the optimal initial target bone model.

Further, determining a matching point corresponding to each target regional point in the optimal initial target bone model, and calculating a transformation relationship between the target regional point and the corresponding matching point specifically include the following steps:

calculating the distance from each target regional point to all points in the optimal initial-target bone model, selecting a point corresponding to the minimum distance as the corresponding matching point of each target regional point in the optimal initial target bone model; and calculating a transformation relationship between the target regional point and the corresponding matching point according to spatial coordinates of each target regional point and the corresponding matching point.

Further, performing spatial transformation on all points in the optimal initial target bone model according to the transformation relationship to obtain a target bone model specifically includes the following steps:

according to the transformation relationship, performing spatial transformation on all points in the optimal initial target bone model by means of a TPS (Thin Plate Splines) interpolation method to obtain a final target bone model.

Further, the sample feature point and the target feature point specifically include anatomical landmark points on the sample bone model and real bones, and/or convex points or concave points in irregular regions of bones.

Further, selecting target feature points and target regional points on real bones of a patient and recording positions of the target feature points and the target regional points under an image coordinate system specifically include the following steps:

selecting target feature points and target regional points on the real bones of the patient using a positioning tool and a needle type registration tool, and recording the positions of the target feature points and the target regional points under an image coordinate system by an optical camera.

In another aspect, a system for constructing a bone model disclosed by the present disclosure includes the following steps:

a sample model acquisition and marking module, configured to acquire multiple sample bone models, and to mark sample feature points in the sample bone models;

a target point selection module, configured to select target feature points and target regional points on real bones of a patient, and to record positions of the target feature points and the target regional points under an image coordinate system, where the target feature points are points, corresponding to the sample feature points, on the real bones of the patient, and the target regional points are points in a key region needed for bone model construction;

a registration module, configured to perform spatial transformation on the target feature points and the target regional points under the image coordinate system according to the positions of the target feature points and the target regional points under the image coordinate system, so as to register the target feature points with the sample feature points in any sample bone model under a same coordinate system;

an initial target bone model construction module, configured to formulate an impact factor assignment strategy for assigning an impact factor for each sample bone model, to linearly combine all sample bone models according to the impact factor assignment strategy to construct an initial target bone model, and to determine initial feature points corresponding to the target feature points in the initial target bone model;

an optimal initial target bone model determination module, configured to adjust the impact factor assignment strategy according to distance between the initial feature points and the corresponding target feature points, to select an impact factor assignment strategy corresponding to the minimum distance as an optimal impact factor assignment strategy, and to determine an optimal initial target bone model according to the optimal impact factor assignment strategy; and a target bone model forming module, configured to determine a matching point corresponding to each target regional point in the optimal initial target bone model, to calculate a transformation relationship between the target regional point and the corresponding matching point, and to perform spatial transformation on all points in the optimal initial target bone model according to the transformation relationship, so as to obtain a final target bone model.

In another aspect, a computer device is further disclosed, including a memory and a processor. The memory is configured to store a computer program, and the computer program, when executed by a processor, enables the processor to execute the steps of any method above.

In another aspect, a computer readable storage medium is further disclosed, the computer readable storage medium is configured to store a computer program. The computer program, when executed by a processor, enables the processor to execute the steps of any method above.

By adopting the technical solution, the present disclosure has the following beneficial effects:

In the method for constructing a bone model disclosed by the present disclosure, the target feature point and target regional point positions on the real bones of the patient can be recorded only using a simple positioning tool and an optical camera, an impact factor assignment strategy is formulated to assign impact factors to the sample bone models, all the sample bone models are linearly combined to construct an initial target bone model, and then the impact factor assignment strategy is adjusted according to the distance between the initial feature points on the initial target bone model and the corresponding target feature points, so as to determine the optimal initial target bone model with the smallest difference from the target bone model. Then, the details of the optimal initial target bone model are adjusted through the target regional points to accurately obtain the final target bone model for simulating the real bones of the patient. The existing sample bone models can be flexibly and reasonably utilized, the operation and calculation steps are simple, and the bone surface information of the patient does not need to be obtained through CT in advance, such that the radiation damage of CT to the patient can be effectively avoided, and the economic burden of the patient can be reduced, the construction efficiency of the bone model is improved, and the diagnosis and treatment time is shortened. Meanwhile, in the process of model construction, there is no need to pierce the cartilage of the patient to collect information, the human errors in collection can be effectively avoided, the construction accuracy of the target bone model can be improved, thus helping doctors make more accurate preoperative plans and providing more effective treatment effects for the patient.

BRIEF DESCRIPTION OF THE DRAWINGS

To describe the technical solutions of the present disclosure or in the prior art more clearly, the following briefly introduces the accompanying drawings required for describing the embodiments or the prior art. Apparently, the accompanying drawings in the following description show merely some embodiments of the present disclosure, and those of ordinary skill in the art may still derive other drawings from these accompanying drawings without creative efforts.

In the drawings.

Figure 1:
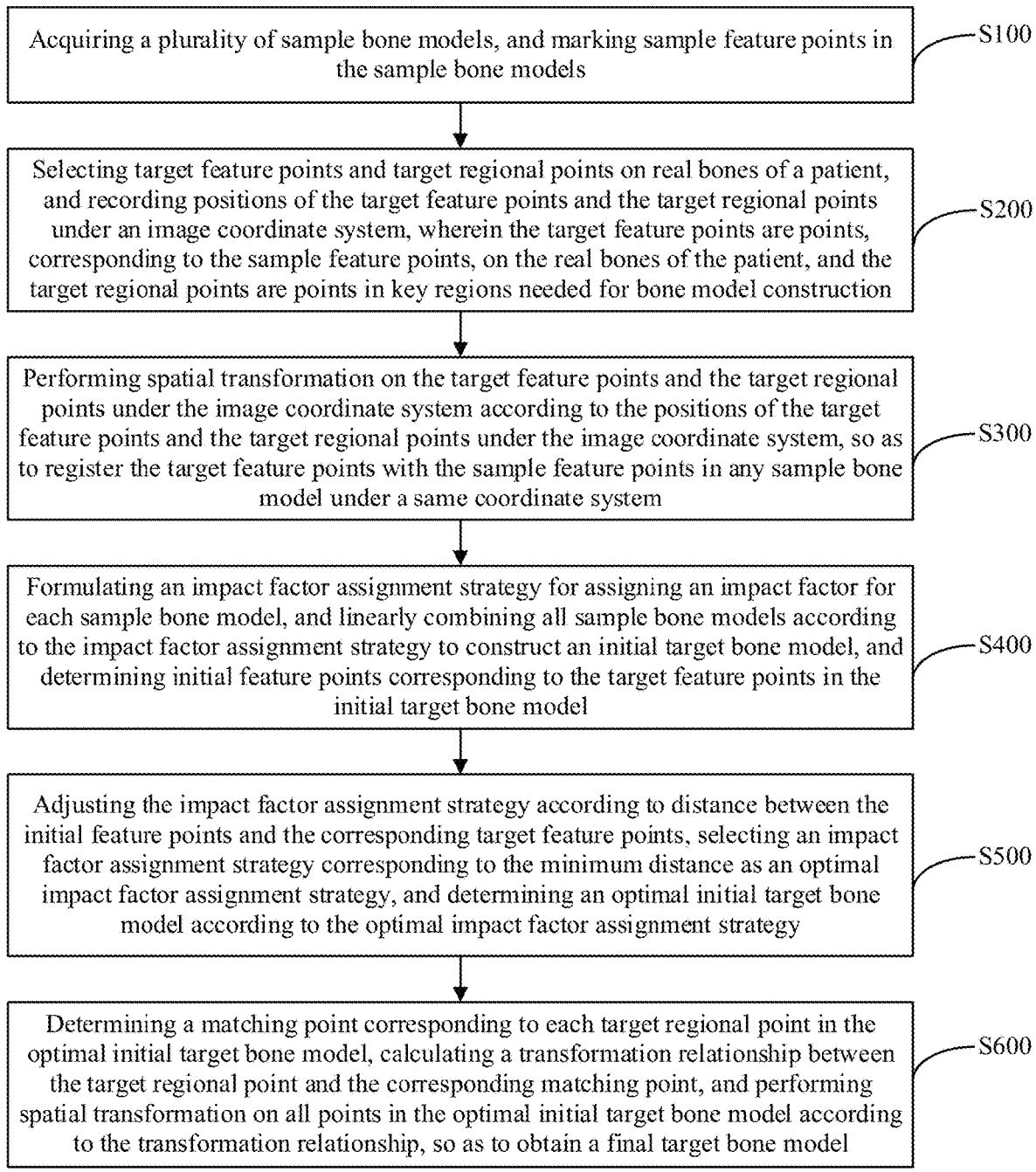
FIG. 1 is a flow chart of a method for constructing a bone model according to an embodiment.

In the drawings: 100—sample model acquisition and marking module; 200—target point selection module; 300—registration module; 400—initial target bone model construction module; 500—optimal initial target bone model determination module; 600—target bone model formation module.

DETAILED DESCRIPTION OF THE EMBODIMENTS

The following clearly and completely describes the technical solutions in the embodiments of the present disclosure with reference to the accompanying drawings in the embodiments of the present disclosure. Apparently, the described embodiments are merely a part rather than all of the embodiments of the present disclosure. All other embodiments obtained by a person of ordinary skill in the art based on the embodiments of the present disclosure without creative efforts shall fall within the protection scope of the present disclosure.

As shown in FIG. 1, in an embodiment, a method for constructing a bone model is provided, specifically including the following steps:

S100. Multiple sample bone models are acquired, and sample feature points in the sample bone models are marked.

During specific implementation, a sample model database can be established, and multiple different three-dimensional sample bone models acquired are stored in the database. Each sample bone model is topologically reconstructed to generate multiple topologically connected model points on the surface of each sample bone model, so as to eliminate irregular surface and holes and facilitate subsequent processing. A unique ID number can be given to each model point, and sample feature points are marked in each sample bone model. Specifically, the sample feature points may be bone marker points with special anatomical significance, or convex points or concave points in irregular regions of the bones.

S200. Target feature points and target regional points are selected on real bones of a patient, and positions of the target feature points and the target regional points under an image coordinate system are recorded, where the target feature points are points corresponding to the sample feature points on the real bones of the patient, and the target regional points are points in key regions needed for bone model construction.

During specific implementation, a positioning tool may be installed on the real bones of the patient, which is placed in the field of view of an optical camera. A needle type registration tool is used to select the target feature points in turn on real bones of the patient in the real world according to the guidance process. When every feature point is selected, a spatial position of the feature point is recorded and saved using the image coordinate system of the optical camera. These features points are points in one-to-one correspondence with the positions of the sample feature points on the real bones of the patient, and multiple target regional points are continuously selected in the surface of the real bones of the patient in turn according to this process. These target regional pints may be points mainly located in the articular cartilage surface, which affect the surgical planning results and are in key regions required for bone model construction, and the spatial position of each target regional point in the image coordinate system is also recorded and saved using the optical camera.

The optical camera is an imaging device based on optical principle, and is configured to capture and record images of an object and a position of the object in the space. In medical imaging and computer-aided surgery, a binocular optical camera is often used to achieve accurate three-dimensional calibration. The binocular optical camera includes two camera sensors, and the distance and angle between the two camera sensors are similar to human eyes. By means of two perspectives for capturing the object simultaneously, the binocular optical camera can calculate three-dimensional coordinates of the object in space. Specifically, in this embodiment, the optical camera may be a near infrared binocular camera.

The positioning tool is a device for tracking the position of the object in real space. In the medical imaging and computer-aided surgery, the positioning tool may be mounted on the bone of the patient or other body parts. Specifically, in this embodiment, the positioning tool may be a passive reflective ball or an active infrared light emitting ball. The passive reflective ball is composed of a group of reflective balls capable of reflecting light. When the optical camera irradiates light on these reflective balls, the reflective balls may reflect light back to the camera, so the camera can detect the positions of the reflective balls. By calculating relative positions of these reflective balls in space, the position and posture of the bones can be accurately determined. The active infrared light emitting ball is different from the passive reflective ball. The active infrared light emitting ball can emit infrared ray autonomously. The positioning tool includes a group of infrared light emitting balls, which can emit infrared rays outward. The optical camera can detect these infrared rays, thus determining the positions of the infrared light emitting balls in space. Similarly, by calculating the relative positions of these infrared light emitting balls, the position and posture of the bones can be accurately determined.

Through the cooperative use of the optical camera and the positioning tool, the position and posture of the bones of the patient and internal points in the bones in space can be accurately measured and positioned to provide more accurate data and information for doctors, and thus the doctors can perform surgical planning more accurately, and the success rate and effect of the surgery can be improved.

S300. Spatial transformation is carried out on the target feature points and the target regional points under the image coordinate system according to the positions of the target feature points and the target regional points under the image coordinate system, so as to register the target feature points with the sample feature points in any sample bone model under a same coordinate system.

During specific implementation, as the positions of the target feature points and the target regional points under the image coordinate system are recorded by the optical camera, and the sample bone model and the feature points thereof are both located in a model spatial coordinate system, the coordinate systems in which the target feature points and the target regional points as well as the sample bone model are located are inconsistent, and subsequent comparison processing cannot be carried out. Therefore, it is necessary to transform the target feature points and the target region points as well as the sample bone model into the same coordinate system for alignment and registration through spatial transformation. Moreover, because the target feature points are in one-to-one correspondence with the sample feature points of the sample bone model in space, a reference standard for registration is provided, that is, by registering the target feature points with the sample feature points in any sample bone model, the optimal alignment of the target feature points and the target regional points with the sample bone model in the same coordinate system can be achieved.

More specifically, the target feature points and the target regional points under the image coordinate system can be subjected to spatial transformation through an ICP registration algorithm, so as to register the target feature points with the sample feature points in any sample bone model under the same coordinate system. The ICP registration, the full name of Iterative Closest Point registration, is an efficient and accurate 3D scanning data registration method.

S400. An impact factor assignment strategy is formulated for assigning an impact factor for each sample bone model, and all sample bone models are linearly combined according to the impact factor assignment strategy to construct an initial target bone model, and initial feature points corresponding to the target feature points are determined in the initial target bone model.

S500. The impact factor assignment strategy is adjusted according to the distance between the initial feature points and the corresponding target feature points, an impact factor assignment strategy corresponding to the minimum distance is selected as an optimal impact factor assignment strategy, and an optimal initial target bone model is determined according to the optimal impact factor assignment strategy.

During specific embodiment, in order to obtain the final target bone model for simulating the real bone condition of the patient, an initial model can be constructed based on the existing sample bone model, and then the initial model can be modified and adjusted according to the real bone condition of the patient, so as to obtain a final target bone model.

In the process of constructing the initial model based on the sample bone model, due to great individual differences between the sample bone models, it is impossible to determine which sample bone model is the best for constructing the initial model, and meanwhile, if the initial model is constructed only based on a single sample model, the constructed model can only have the model characteristics of the single sample model, which is not representative and universal, and there may be a great difference between the constructed initial model and the real bones of the patient, and a large amount of work is required for adjustment and modification work later, which is not conducive to the efficient and accurate construction of the target bone model.

Therefore, in this embodiment, by formulating the impact factor assignment strategy, the corresponding impact factor is assigned to each sample bone model. According to the impact factor assignment strategy, all sample bone models are linearly combined, and the model obtained after linear combination is taken as the constructed initial target bone model, such that the initial model can integrate model characteristics of all sample bone models, the problem that the initial model constructed only based on a single sample model is not representative is solved, and a premise is provided for the efficient and accurate construction of the subsequent target bone model.

According to the impact factor assignment strategy, all the sample bone models are linearly combined, that is, all the model points in each sample bone model are weighted and summed to construct the initial target bone model. Therefore, in the initial target bone model, there are corresponding initial feature points formed by the addition of sample feature points, moreover, because the sample feature points correspond to the target feature points one by one, the initial feature points also correspond to the target feature points one by one, specifically, the initial feature points and the target feature points may be mutually matched with and correspond to each other through IDs of the points in the models.

The distance between the initial feature point in the initial target bone model and the target feature point can be used to represent a position difference between the initial feature point in the initial target bone model and the target feature point. The smaller the distance, the closer the initial feature point in the initial target bone model is to the target feature point on the real bones of the patient. In other words, the closer the initial target bone model is to the target bone model to be constructed for simulating the real bones of the patient, the more accurate the real bone condition of the patient can be simulated, and the degree of further adjustment and optimization is less.

Therefore, in this embodiment, the impact factor assignment strategy is further adjusted according to the distance between the initial feature point and the corresponding target feature point, and the impact factor assignment strategy corresponding to the minimum distance is taken as the optimal impact factor assignment strategy. According to the optimal impact factor assignment strategy, the sample bone models are linearly combined to obtain the optimal initial target bone model with the smallest difference from the final target bone model, and then the most accurate target bone model can be obtained only by slightly adjusting the difference details of the optimal initial target bone model, so as to further improve the construction accuracy and construction efficiency of the target bone model.

S600. A matching point corresponding to each target regional point is determined in the optimal initial target bone model, a transformation relationship between the target regional point and the corresponding matching point is calculated, and all points in the optimal initial target bone model are subjected to spatial transformation according to the transformation relationship, so as to obtain a final target bone model.

During specific implementation, after the optimal initial target bone model with the smallest difference from the target bone model is selected through the correspondence between the target feature points and the initial feature points, the positions of the target regional points on the optimal initial target bone model may still have some deviation from real positions in the final target bone model due to the fact that the target regional points still have no mapping relationship on the optimal initial target bone model, so it is necessary to further reduce the position deviation of the target regional points to further optimize and adjust positions of all points on the optimal initial target bone model, thus obtaining the most accurate target bone model. Therefore, in this embodiment, a matching point corresponding to each target regional point can be first found in the optimal initial target bone model, a transformation relationship between the target regional point and the corresponding matching point is calculated, and then all points in the optimal initial target bone model are subjected to spatial transformation through this transformation relationship, so as to obtain the most accurate target bone model.

Specifically, the point corresponding to the minimum distance can be selected by calculating the distance from each target regional point to all points in the optimal initial target bone model, and the point corresponding to the minimum distance is used as the corresponding matching point of each target regional point in the optimal initial target bone model.

A transformation relationship between the target regional point and the corresponding matching point is calculated according to spatial coordinates of each target regional point and the corresponding matching point.

According to the transformation relationship, all points in the optimal initial target bone model are subjected to spatial transformation by means of a TPS interpolation method, so as to obtain a target bone model.

According to the model for constructing the bone model disclosed by above embodiment, the target feature point and target regional point positions on the real bones of the patient can be recorded only using a simple positioning tool and an optical camera, an impact factor assignment strategy is formulated to assign impact factors to the sample bone models, all the sample bone models are linearly combined to construct an initial target bone model, and then the impact factor assignment strategy is adjusted according to the distance between the initial feature points on the initial target bone model and the corresponding target feature points, so as to determine the optimal initial target bone model with the smallest difference from the target bone model. Then, the details of the optimal initial target bone model are adjusted through the target regional points to accurately obtain the final target bone model for simulating the real bones of the patient. The existing sample bone models can be flexibly and reasonably utilized, the operation and calculation steps are simple, and the bone surface information of the patient does not need to be obtained through CT in advance, such that the radiation damage of CT to the patient can be effectively avoided, and the economic burden of the patient can be reduced, the construction efficiency of the bone model is improved, and the diagnosis and treatment time is shortened. Meanwhile, in the process of model construction, there is no need to pierce the cartilage of the patient to collect information, the human errors in collection can be effectively avoided, the construction accuracy of the target bone model can be improved, thus helping doctors make more accurate preoperative plans and providing more effective treatment effects for the patient.

The following illustrates the method for constructing the bone model by taking the specific implementation process of constructing a femoral condyle three-dimensional model as an example.

Sample bone model acquisition process:

A sample femoral model database is established, including multiple femoral condyle three-dimensional models, each model has been topologically reconstructed to eliminate irregular surfaces and holes, so as to facilitate subsequent comparison and selection.

Step One. Gridding Processing
  a. A sample femoral condyle three-dimensional model is selected.
  b. The selected femoral condyle model is transformed into a triangular grid model using 3D modeling software or algorithm.
  c. The grid model after processing is saved as a new file for subsequent processing.

Figure 2:
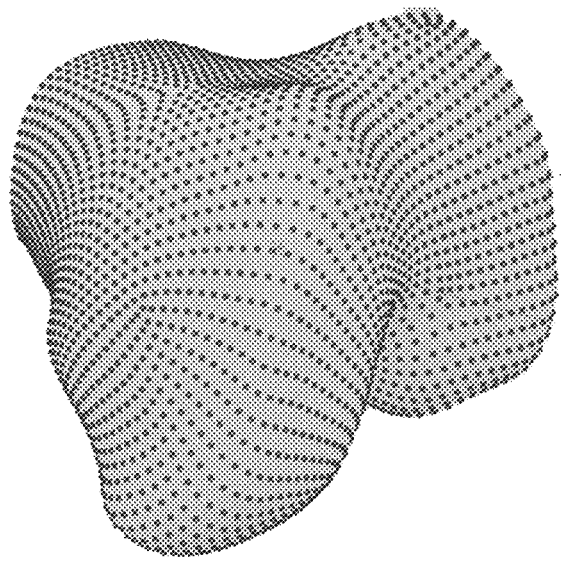
FIG. 2 is a schematic diagram of topology reconstruction of a sample bone model according to an embodiment.

Step Two. Topological Reconstruction
  a. Grid editing software, such as MeshLab, Blender, is opened.
  b. The processed femoral condyle grid model is imported.
  c. A topological structure of the grid model is adjusted and edited using tools and functions in the grid editing software, thus making topological structures of model points same.
  d. The topologically reconstructed grid model is exported and the saved as a new file, where a schematic diagram of the topological reconstruction of the sample bone model is as shown in FIG. 2.

Figure 3:
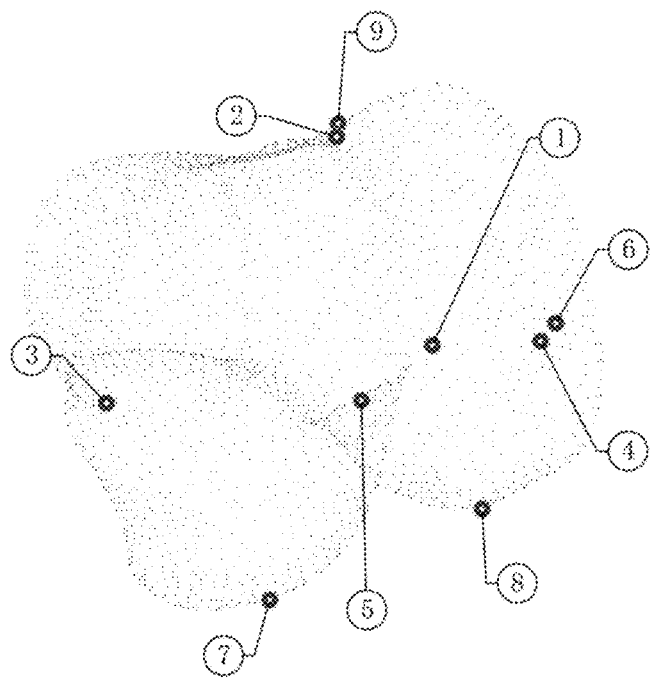
FIG. 3 is a schematic diagram of sample feature point extraction in a sample bone model according to an embodiment.

Step Three. Feature Point Extraction
  a. Sample feature points in the femoral condyle model after topological reconstruction are extracted using feature point extraction algorithms (such as SIFT (Scale-invariant feature transform), Harris corner, FAST (Features from accelerated segment test) corner, Saliency Detection, etc.), where a schematic diagram of sample feature point extraction is shown in FIG. 3, and the extracted sample feature points may be point 1-patella trochlea origin, point 2-patella trochlea end point, point 3-medial epicondyle convex point, point 4-lateral supracondylar convex point, point 5-medial distal high point, point 6-lateral distal high point, point 7-medial posterior condyle low point, point 8-lateral posterior condyle low point, and point 9-high point of the intersection of anterior condyle and diaphysis.
  B. The extracted sample feature points are saved as a separate file for subsequent processing.

Step Four. Model Resampling
  a. The number of points in each sample bone model is adjusted to the same using a model resampling algorithm, such as a grid sampling algorithm, a point cloud down-sampling algorithm, a grid or point cloud interpolation algorithm.
  b. The resampled model is exported and then saved as a new file.

Figure 4:
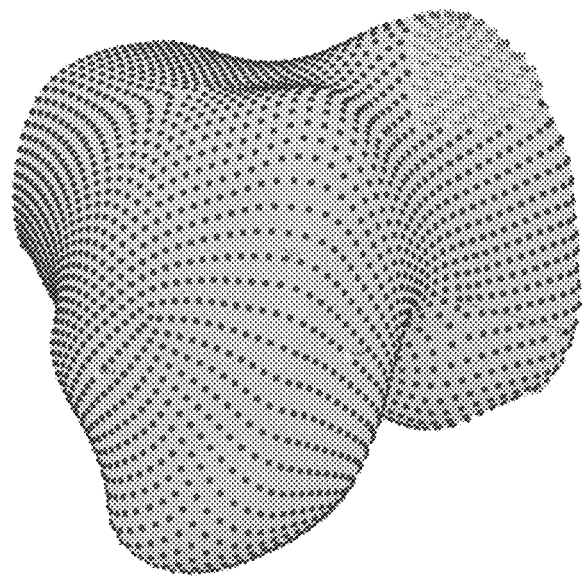
FIG. 4 is a schematic diagram of ID number in a sample bone model according to an embodiment.

Step Five. Point ID Number Unification
  a. The points in all models are numbered uniformly to ensure that the sample feature points at the same position in all models have the same ID number, where a schematic diagram of the femoral condyle three-dimensional model after ID numbering is shown in FIG. 4.
  b. The numbered model is exported and then saved as a new file.

Figure 5:
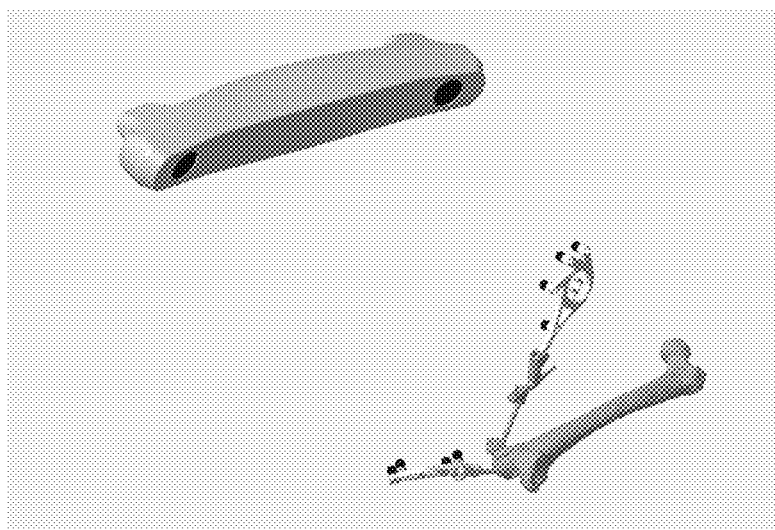
FIG. 5 is a schematic diagram of an optical camera, a positioning tool, and a needle type registration tool according to an embodiment.

Target feature point and target regional point selection process:

Preparation Work:
  a. The patient is arranged in a proper position to ensure that a femoral condyle region of the real bones of the patient can be touched.
  b. A binocular optical camera, a positioning tool (e.g., passive reflective balls or active infrared light emitting balls) and a needle registration tool and other devices are prepared, where a schematic diagram of the optical camera, the positioning tool and the needle type registration tool are as shown in FIG. 5.

Positioning Tool Mounting
  a. A femur positioning tool is mounted on the femoral condyle of the patient to ensure that the positioning tool can be stably fixed in place.
  b. A position of the binocular optical camera is adjusted to make the positioning tool located in the field of view of the camera.

Target Feature Point Selection
  a. Target feature points are selected in turn in the real femoral condyle of the patient in the real world by the needle type registration tool according to the guidance process to ensure that each target feature point is correctly selected in the femoral condyle, where the selected target feature points are 9 points consistent with the above sample feature points 1-9.
  b. Under an image coordinate system of the optical camera, a spatial position of each target feature point is recorded and saved in a data list.

Figure 6:
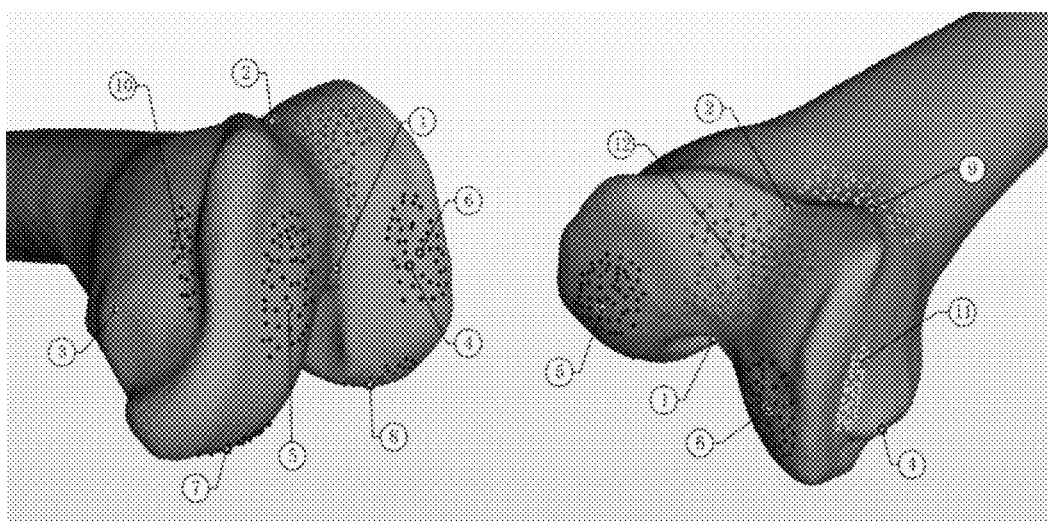
FIG. 6 is a schematic diagram of selection of a target feature point and target regional point of real femoral condyle of a patient according to an embodiment.

Target Regional Point Selection:
  a. Multiple target regional points are continuously selected in turn on the surface of the real femoral condyle of the patient according to the guidance process. the target regional points are points mainly located on the articular cartilage surface and points which affect the surgical planning results and are in a connection region of medial and lateral condyles, the anterior condyle of femur and the femoral shaft required for bone model construction, such as a region 10-lateral supracondylar regional point, a region 11-medial supracondylar regional point, and a region 12-patellar trochlea regional point as shown in FIG. 6.
  b. The spatial position of each target regional point is recorded and saved in the data list.

The schematic diagram of the selection of the target feature point and the target regional point of real femoral condyle of the patient is as shown in FIG. 6.

Figure 7:
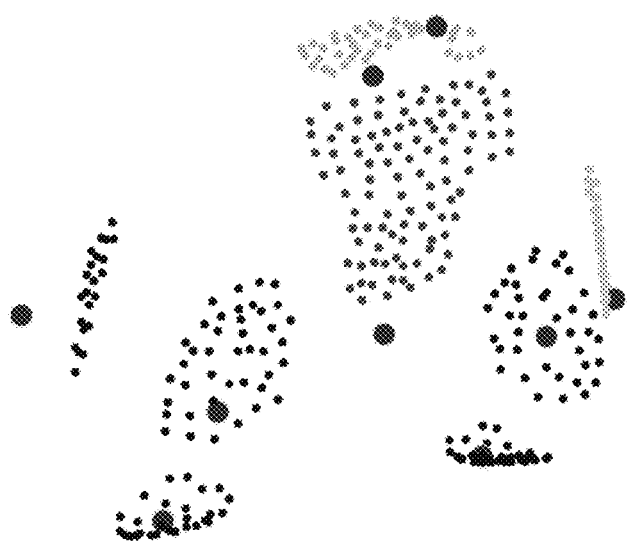
FIG. 7 is a schematic diagram showing positions of target feature points and target regional points of real femoral condyle of a patient according to an embodiment.

Data Saving and Analysis
a. The spatial position data of all target feature points and target regional points are imported into data processing software, e.g., MATLAB or Python, where a specific schematic diagram of positions of the target feature points and the target regional points under the image coordinate system is as shown in FIG. 7.
b. The acquired data are processed and analyzed, so as to provide reference for subsequent surgery planning and model registration.

ICP Registration

The key task of ICP registration is to match the target feature points under the image coordinate system with the sample feature points of any femoral condyle model A in the database. By means of the ICP (Iterative Closest Point) algorithm, the target feature points and the target regional points in a target bone model to be generated can be subjected to movement and rotational spatial transformation, so as to reach the optimal alignment state with the model A in the database under the same coordinate system, and then the next step of determining the optimal initial target bone model can be executed.

Optimal Initial Target Bone Model Determination

A distance mean between the target feature point and an initial feature point of a corresponding ID of the initial target bone model is calculated. An initial target bone model with the lowest distance mean is used as the optimal initial target bone model. This optimal initial target bone model has the smallest difference from the target feature point at the position of the initial feature point. This optimal initial target bone model is used for subsequent model adjustment, so as to further optimize the model to match the target feature point and the target regional point of the target bone model.

Specific steps of determining the optimal initial target bone model are as follows:
1. An optimal initial target bone model variable is initialized for storing the constructed optimal initial target bone model.
2. A minimum distance mean variable is initialized, and a minimum distance mean is set, which can be set as a larger value for storing the minimum distance mean.
3. The impact factor assignment strategy is traversed and searched by means of a search strategy:
a. For the currently searched impact factor assignment strategy, all sample bone models are linearly combined to construct a current initial target bone model, and current initial feature points corresponding to the target feature points are determined in the current initial target bone model; and
a distance sum variable is initialized for calculating a distance sum between the target feature points and the current initial feature points.
b. Each target feature point is traversed:
i. Euclidean distance between a current target feature point and the current initial feature point is calculated;
ii. the calculated Euclidean distance is accumulated into the distance sum variable.
c. The distance sum variable is divided by the number of the target feature points to calculate a distance mean corresponding to the current impact factor assignment strategy.
d. The distance mean corresponding to the current impact factor assignment strategy is compared with the minimum distance mean:
i. if the distance mean corresponding to the current impact factor assignment strategy is less than the minimum distance mean, the current initial target bone model is stored in the optimal initial target bone model variable, and the minimum distance mean variable is updated to the distance mean corresponding to the current impact factor assignment strategy.
4. After completing the search of the impact factor assignment strategy, the model stored in the optimal initial target bone model variable is used as the optimal initial target bone model.

Model Optimization and Adjustment

At this time, because the target regional points do not have a mapping relationship on the optimal initial target bone model yet, the positions of the target regional points on the optimal initial target bone model may still have some deviations from the real positions on the final target bone model. In order to further reduce the position deviation of the target regional point, it is necessary to further optimize and adjust the positions of all points on the optimal initial target bone model, so as to obtain the most accurate target bone model.

At first, the correspondence between the target feature points and the initial feature points in the optimal initial target bone model is known, but the correspondence between the target regional points and the optimal initial target bone model is unknown, so it is necessary to calculate the correspondence between the target region points and the optimal initial target bone model first.

A. Calculation of Correspondence of Target Regional Points

For each target regional point, a point, closest to the target regional point, on the surface of the optimal initial target bone model needs to be found as the matching point, which can be achieved by calculating the Euclidean distance from the target regional point to all points on the surface of the optimal initial target bone model, and then the point with the shortest distance is used as the matching point. Through the above ways, one corresponding matching point can be found for each target regional point, thus establishing a corresponding transformation relationship between the target regional point and the optimal initial target bone model.

A calculation equation for the Euclidean distance is as follows:

$$\rho = \sqrt{(x_2 - x_1)^2 + (y_2 - y_1)^2 + (z_2 - z_1)^2} \quad (1)$$

$(x_1, y_1, z_1)$ represents spatial coordinates of the target regional point, and $(x_2, y_2, z_2)$ represents spatial coordinates of the point of the optimal initial target bone model.

b. Spatial Transformation

According to the transformation relationship calculated in the previous step, all points in the optimal initial target bone model are subjected to spatial transformation to further optimize and adjust the optimal initial target bone model, and thus the most accurate target bone model can be obtained. In order to achieve this target, a thin plate spline (TPS) method can be used.

The TPS interpolation method is an interpolation and registration method, and this function is smooth and easy to calculate in the global scope, and has been widely used in various data registrations and fitting applications. TPS transformation can be defined as a smooth mapping f from $R^3$ to $R^3$ for a group of target regional points with known correspondence and matching points on the surface of the optimal initial target bone model. Taking the target regional points and the matching points $\{L_{Ri}, L_{Ti}\}$, i=1, 2, . . . , m on the surface of the optimal initial target bone model as control points, minimizing the following bending energy function E (f) by TPS has the following interpolation conditions:

$$E(f) = \int_{R^3}\left(\left(\frac{\partial^2 f}{\partial x^2}\right)^2 + \left(\frac{\partial^2 f}{\partial y^2}\right)^2 + 2\left(\frac{\partial^2 f}{\partial xy}\right)^2 + 2\left(\frac{\partial^2 f}{2xz}\right)^2 + 2\left(\frac{\partial^2 f}{2yz}\right)^2\right)dxdydx, \quad (2)$$

$$\text{s.t. } f(L_{T_i}) = L_{R_i}, i = 1, 2, \ldots, M$$

TPS may be decomposed into affine and non-affine components, that is $$f(P) = Pd + \phi(P)\Lambda \quad (3)$$

where P is a point with homogeneous coordinate representation on a 3D surface of the optimal initial target bone model, d is a 4×4 homogeneous affine transformation matrix, A is an M×4 non-affine warping coefficient matrix, and $\phi_{(P)}=(\phi_{1(P)}, \phi_{2(P)}, \ldots, \phi_{M(P)})$ is a 1×M kernel vector of the TPS, which is in the form of $\phi_{k(P)}=|P-L_{Tk}|$.

If the requirements of the interpolation conditions in equation (1) are not strict, the following energy functions can be minimized to find an optimal solution:

$$\overline{E}(\lambda, \Lambda, d) = \frac{1}{M}\sum_{j=1}^{M}\|f(L_{Ti} - L_{Ri})\| + \lambda E(f) \quad (4)$$

λ is a smooth regularization term. If λ is equal to 0, the interpolation conditions in equation (1) are strictly satisfied. The parameters d and Λ of TPS can be obtained by solving the following linear equations:

$$\begin{pmatrix} \Phi & L_R \\ L_R^T & 0 \end{pmatrix}\begin{pmatrix} \Lambda \\ d \end{pmatrix} = \begin{pmatrix} L_T \\ 0 \end{pmatrix} \quad (5)$$

Φ is an M×M matrix, a component of which is $\Phi_{KI}=|L_{TK}-L_{TI}|$, and $L_R$ is an M×4 matrix, each row is homogeneous coordinates of point $L_{Ri}$, and i=1, 2, ..., M, $L_R$ has the same meaning.

Figure 8:
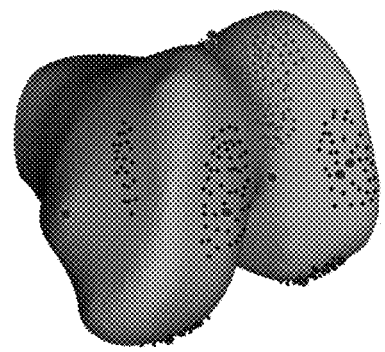
FIG. 8 is a schematic diagram of a finally obtained target bone model according to an embodiment.

After solving the transformation relationship, the variables obtained by correlation are brought in according to Equation (3), and all points on the optimal initial target bone model are' input in turn to obtain new points on the optimal initial target bone model under the transformation relationship, and thus the optimal initial target bone model can be further optimized and enhanced to obtain the target bone model, and the final target bone model is shown in FIG. 8.

Figure 9:
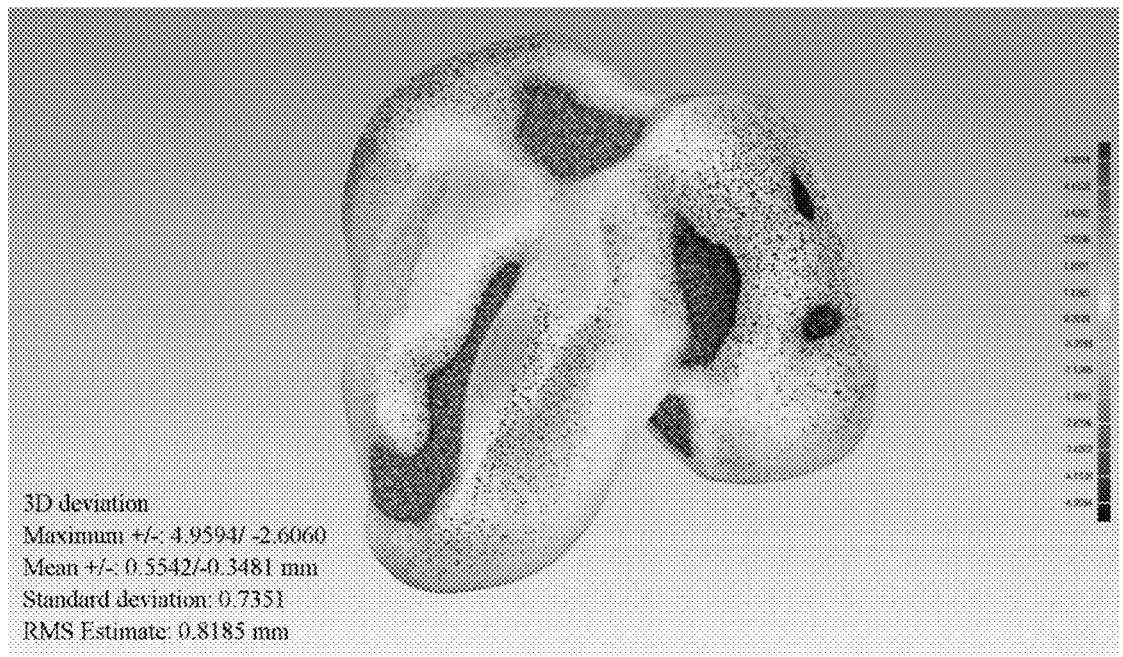
FIG. 9 is a schematic diagram of comparative analysis of a target bone model and a real bone model according to an embodiment.

In addition, in this embodiment, the target bone model and the real bone model are compared and analyzed, and a comparative analysis schematic diagram is as shown in FIG. 9. It can be seen that a deviation between the target bone model obtained through the method for constructing the bone model and the real bone model is kept within a small range, the constructed target bone model can simulate and replace the real bones of the patient, that is, the method for constructing the bone model can effectively achieve the technical effect of accurately constructing the bone model.

Figure 10:
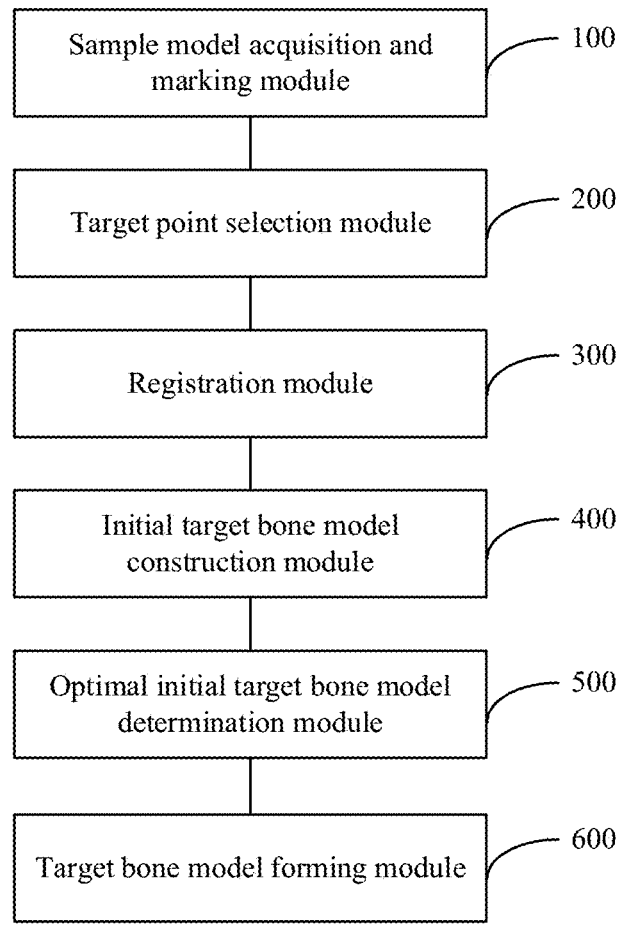
FIG. 10 is a structural block diagram of a system for constructing a bone model according to an embodiment.

In another aspect, as shown in FIG. 10, in an embodiment, a system for constructing a bone model is provided, including:

a sample model acquisition and marking module 100, configured to acquire a plurality of sample bone models, and to mark sample feature points in the sample bone models;

a target point selection module 200, configured to select target feature points and target regional points on real bones of a patient, and to record positions of the target feature points and the target regional points under an image coordinate system, wherein the target feature points are points, corresponding to the sample feature points, on the real bones of the patient, and the target regional points are points in a key region needed for bone model construction;

a registration module 300, configured to perform spatial transformation on the target feature points and the target regional points under the image coordinate system according to the positions of the target feature points and the target regional points under the image coordinate system, so as to register the target feature points with the sample feature points in any sample bone model under a same coordinate system;

an initial target bone model construction module 400, configured to formulate an impact factor assignment strategy for assigning an impact factor for each sample bone model, to linearly combine all sample bone models according to the impact factor assignment strategy to construct an initial target bone model, and to determine initial feature points corresponding to the target feature points in the initial target bone model;

an optimal initial target bone model determination module 500, configured to adjust the impact factor assignment strategy according to distance between the initial feature points and the corresponding target feature points, to select an impact factor assignment strategy corresponding to the minimum distance as an optimal impact factor assignment strategy, and to determine an optimal initial target bone model according to the optimal impact factor assignment strategy; and a target bone model forming module 600, configured to determine a matching point corresponding to each target regional point in the optimal initial target bone model, to calculate a transformation relationship between the target regional point and the corresponding matching point, and to perform spatial transformation on all points in the optimal initial target bone model according to the transformation relationship, so as to obtain a final target bone model.

It should be noted that other corresponding descriptions of each functional module involved in the system for constructing the bone model provided by this embodiment may refer to the corresponding descriptions of the methods in the above embodiments, and thus are not repeated here.

In another aspect, in one embodiment, a computer readable storage medium is further disclosed, which is configured to store a computer program. The computer program, when executed by a processor, enables the processor to execute the steps of any method above.

In another aspect, in one embodiment, a computer device is further disclosed, including a memory and a processor. The memory is configured to store a computer program, and the computer program, when executed by a processor, enables the processor to execute the steps of any method above.

Figure 11:
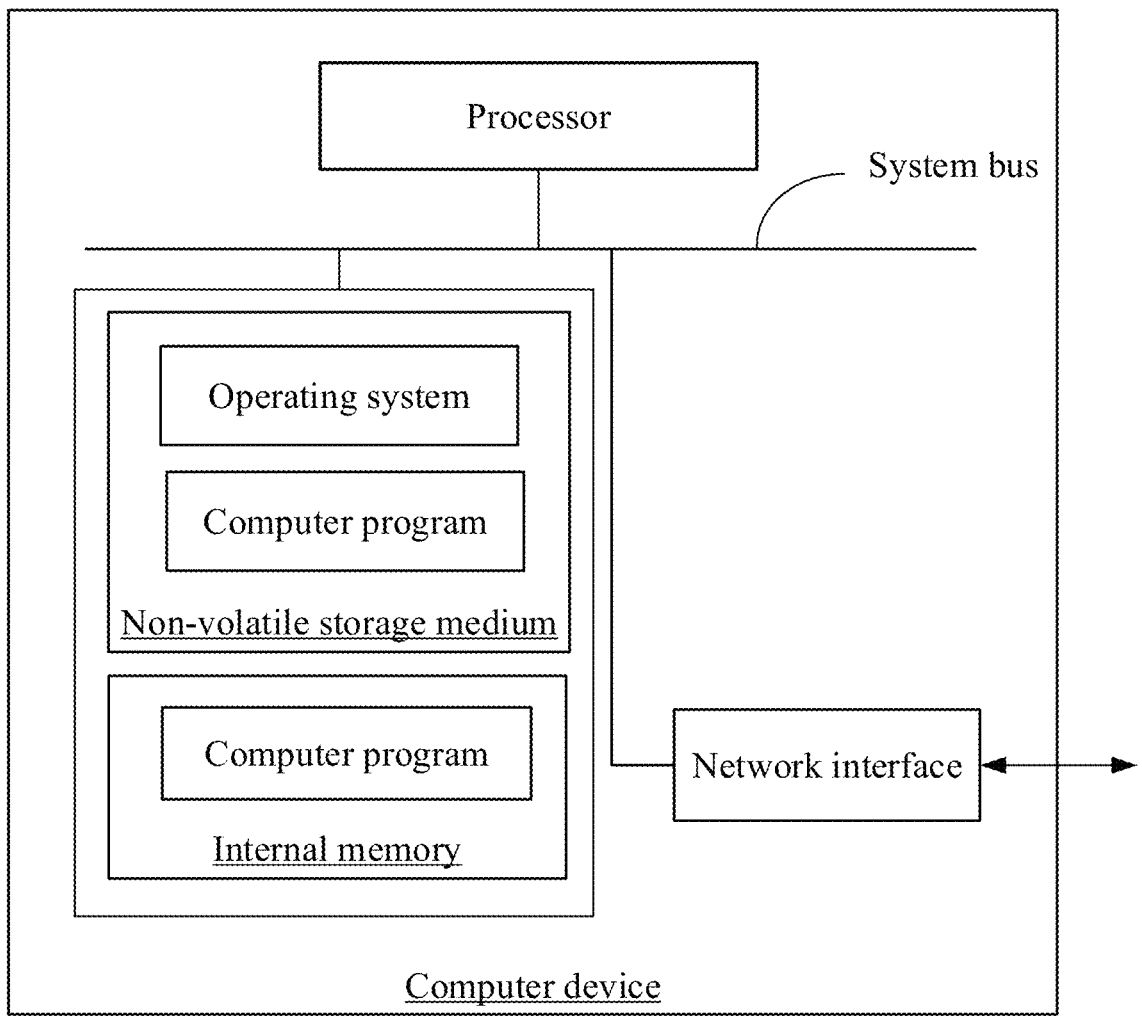
FIG. 11 is a structural block diagram of a computer device according to an embodiment.

FIG. 11 is a diagram of an internal structure of a computer device according to an embodiment. The computer device may specifically be a terminal, or a server. As shown in FIG. 11, the computer device includes a processor, a memory and a network interface which are connected by a system bus. The memory includes a non-volatile storage medium and an internal memory. The non-volatile storage medium of the computer device is configured to store an operating system and a computer program. The computer program, when executed by the processor, can enable the processor to achieve the above method for constructing the bone model. The internal memory may also be configured to store the computer program. The computer program, when executed by a processor, enables the processor to execute the above method for constructing the bone model. Those skilled in the part may understand that the structure shown in FIG. 11 is only a block diagram of a part of the structure related to the scheme of the present disclosure, and does not constitute a limitation on the computer device to which the scheme of the present disclosure is applied. The specific computer device may include more or less components than those shown in the figure, or combine some components, or have different component arrangements.

Those skilled in the art can understand that all or part of the processes in the method for achieving the above embodiments can be completed by instructing related hardware through a computer program, which can be stored in a nonvolatile computer-readable storage medium, and when executed, the program may include the processes of the above-mentioned embodiments. Any reference to memory, storage, database or other media used in the embodiments provided in the present disclosure may include non-volatile and/or volatile memories. The non-volatile memory may include a read-only memory (ROM), a programmable ROM (PROM), an electrically programmable ROM (EPROM), and an electrically erasable programmable ROM (EEPROM) or a flash memory. The volatile memory may include a random-access memory (RAM) or an external cache memory. By way of illustration than limitation, RAM is available in various forms, such as static RAM (SRAM), dynamic RAM (DRAM), synchronous DRAM (SDRAM), double data rate SDRAM (DDRSDRAM), enhanced SDRAM (ESDRAM), synchronous link DRAM (SLDRAM), memory bus (Rambus) direct RAM (RDRAM), and direct memory bus.

The technical features of the above embodiments can be combined at will. In order to make the description concise, not all possible combinations of the technical features in the above embodiments are described. However, it should be considered that these combinations of technical features fall within the scope recorded in this specification provided that these combinations of technical features do not have any conflict.

The foregoing embodiments only describe several implementations of the present disclosure, and their description is specific and detailed, but cannot therefore be understood as a limitation to the patent scope of the present disclosure. It should be noted that for those of ordinary skill in the art, several deformations and improvements can be made without departing from the concept of the present disclosure, all of which fall within the scope of protection of the present disclosure. Therefore, the scope of protection of the patent of the present disclosure shall be subject to the appended claims.

What is claimed is:

1. A method for constructing a bone model, comprising the following steps:
   acquiring a plurality of sample bone models, and marking sample feature points in the sample bone models;
   selecting target feature points and target regional points on real bones of a patient, and recording positions of the target feature points and the target regional points under an image coordinate system, wherein the target feature points are points, corresponding to the sample feature points, on the real bones of the patient, and the target regional points are points in key regions needed for bone model construction;
   performing a first spatial transformation on the target feature points and the target regional points under the image coordinate system according to the positions of the target feature points and the target regional points under the image coordinate system, so as to register the target feature points with the sample feature points in any sample bone model under the image coordinate system;
   formulating an impact factor assignment strategy for assigning an impact factor for each sample bone model, and linearly combining all sample bone models according to the impact factor assignment strategy to construct an initial target bone model, and determining initial feature points corresponding to the target feature points in the initial target bone model;
   adjusting the impact factor assignment strategy according to distances between the initial feature points and the corresponding target feature points, selecting an impact factor assignment strategy corresponding to a minimum distance between the initial feature points and the corresponding target feature points as an optimal impact factor assignment strategy, and determining an optimal initial target bone model according to the optimal impact factor assignment strategy; and
   determining a matching point corresponding to each target regional point in the optimal initial target bone model, calculating a transformation relationship between the target regional point and the corresponding matching point, and performing a second spatial transformation on all points in the optimal initial target bone model according to the transformation relationship, so as to obtain a final target bone model.

2. The method for constructing a bone model according to claim 1, wherein performing spatial transformation on the target feature points and the target regional points under the image coordinate system to make the target feature points register with the sample feature points in any sample bone model under a same coordinate system specifically comprises the following steps:
   performing spatial transformation on the target feature points and the target regional points under the image coordinate system by means of an ICP (Iterative Closest Point) registration algorithm, so as to register the target feature points with the sample feature points in any sample bone model under the same coordinate system.

3. The method for constructing a bone model according to claim 1, wherein adjusting the impact factor assignment strategy according to distance between the initial feature points and the corresponding target feature points, selecting an impact factor assignment strategy corresponding to the minimum distance between the initial feature points and the corresponding target feature points as an optimal impact factor assignment strategy, and determining an optimal initial target bone model according to the optimal impact factor assignment strategy specifically comprise the following steps:
   initializing an optimal initial target bone model variable for storing the constructed optimal initial target bone model;

initializing a minimum distance mean variable, presetting a minimum distance mean, and storing the minimum distance mean in the minimum distance mean variable;

traversing and searching the impact factor assignment strategy through a searching strategy;

for the currently searched impact factor assignment strategy, linearly combining all sample bone models to construct a current initial target bone model, and determining current initial feature points corresponding to the target feature points in the current initial target bone model;

initializing a distance sum variable for calculating a distance sum between the target feature points and the current initial feature points;

traversing each target feature point;

calculating Euclidean distance between a current target feature point and the current initial feature point;

accumulating calculated Euclidean distance into the distance sum variable;

dividing the distance sum variable by the number of the target feature points to calculate the distance mean corresponding to the current impact factor assignment strategy;

comparing the distance mean corresponding to the current impact factor assignment strategy with the minimum distance mean;

if the distance mean corresponding to the current impact factor assignment strategy is less than the minimum distance mean, storing the current initial target bone model in the optimal initial target bone model variable, and updating the minimum distance mean variable to a distance mean corresponding to the current impact factor assignment strategy; and after completing the search of the impact factor assignment strategy, taking the model stored in the optimal initial target bone model variable as the optimal initial target bone model.

4. The method for constructing a bone model according to claim 1, wherein determining a matching point corresponding to each target regional point in the optimal initial target bone model, and calculating a transformation relationship between the target regional point and the corresponding matching point specifically comprise the following steps:

calculating the distance from each target regional point to all points in the optimal initial target bone model, selecting a point corresponding to a minimum distance as the corresponding matching point of each target regional point in the optimal initial target bone model; and calculating a transformation relationship between the target regional point and the corresponding matching point according to spatial coordinates of each target regional point and the corresponding matching point.

5. The method for constructing a bone model according to claim 1, wherein performing spatial transformation on all points in the optimal initial target bone model according to the transformation relationship to obtain a target bone model specifically comprises the following steps:

according to the transformation relationship, performing spatial transformation on all points in the optimal initial target bone model by means of a TPS (Thin Plate Splines) interpolation method to obtain a final target bone model.

6. The method for constructing a bone model according to any claim 1, wherein the sample feature point and the target feature point specifically comprise anatomical landmark points on the sample bone model and real bones, and/or convex points or concave points in irregular regions of bones.

7. The method for constructing a bone model according to claim 1, wherein selecting target feature points and target regional points on real bones of a patient and recording positions of the target feature points and the target regional points under an image coordinate system specifically comprise the following steps:

selecting target feature points and target regional points on the real bones of the patient using a positioning tool and a needle type registration tool, and recording the positions of the target feature points and the target regional points under an image coordinate system by an optical camera.

8. A computer readable storage medium, configured to store computer program, wherein the computer program, when executed by a processor, enables the processor to execute the steps of the method according to claim 1.

9. A computer device, comprising a memory and a processor, wherein the memory is configured to store a computer program, and the computer program, when executed by the processor, enables the processor to execute the steps of the method according to claim 1.

10. A system for constructing a bone model, comprising:

a sample model acquisition and marking module, configured to acquire a plurality of sample bone models, and to mark sample feature points in the sample bone models;

a target point selection module, configured to select target feature points and target regional points on real bones of a patient, and to record positions of the target feature points and the target regional points under an image coordinate system, wherein the target feature points are points, corresponding to the sample feature points, on the real bones of the patient, and the target regional points are points in a key region needed for bone model construction;

a registration module, configured to perform spatial transformation on the target feature points and the target regional points under the image coordinate system according to the positions of the target feature points and the target regional points under the image coordinate system, so as to register the target feature points with the sample feature points in any sample bone model under a same coordinate system;

an initial target bone model construction module, configured to formulate an impact factor assignment strategy for assigning an impact factor for each sample bone model, to linearly combine all sample bone models according to the impact factor assignment strategy to construct an initial target bone model, and to determine initial feature points corresponding to the target feature points in the initial target bone model;

an optimal initial target bone model determination module, configured to adjust impact factor assignment strategy according to distance between the initial feature points and the corresponding target feature points, to select an impact factor assignment strategy corresponding to the minimum distance as an optimal impact factor assignment strategy, and to determine an optimal initial target bone model according to the optimal impact factor assignment strategy; and a target bone model forming module, configured to determine a matching point corresponding to each target regional point in the optimal initial target bone model, to calculate a transformation relationship between the target regional point and the corresponding matching point, and to perform spatial transformation on all points in the optimal initial target bone model according to the transformation relationship, so as to obtain a final target bone model.

* * * * *